(12) United States Patent
Wilde

(10) Patent No.: US 7,584,648 B2
(45) Date of Patent: Sep. 8, 2009

(54) GAS SENSOR CONTAINING A PROTECTIVE TUBE

(75) Inventor: Juergen Wilde, Fellbach (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 11/791,417

(22) PCT Filed: Aug. 26, 2005

(86) PCT No.: PCT/EP2005/054203

§ 371 (c)(1),
(2), (4) Date: Jan. 14, 2008

(87) PCT Pub. No.: WO2006/056493

PCT Pub. Date: Jun. 1, 2006

(65) Prior Publication Data

US 2008/0105030 A1 May 8, 2008

(30) Foreign Application Priority Data

Nov. 23, 2004 (DE) ......................... 10 2004 056 417

(51) Int. Cl.
*G01N 25/00* (2006.01)
*G01R 31/28* (2006.01)

(52) U.S. Cl. .......................... 73/31.05; 73/23.2; 29/593
(58) Field of Classification Search .................. 73/23.2, 73/23.31, 31.05; 29/593, 613
See application file for complete search history.

(56) References Cited

U.S. PATENT DOCUMENTS

| | | | | |
|---|---|---|---|---|
| 4,597,850 A | * | 7/1986 | Takahasi et al. ............. | 204/426 |
| 5,329,806 A | * | 7/1994 | McClanahan et al. ...... | 73/31.05 |
| 6,453,726 B1 | * | 9/2002 | Gutierrez et al. ........... | 73/31.05 |
| 7,434,448 B2 | * | 10/2008 | Weyl et al. .................. | 73/23.31 |
| 7,454,949 B2 | * | 11/2008 | Geier et al. ................. | 73/23.31 |
| 2002/0020210 A1 | * | 2/2002 | Murase et al. ............. | 73/31.05 |
| 2003/0015020 A1 | * | 1/2003 | Geier et al. ................. | 73/23.31 |

FOREIGN PATENT DOCUMENTS

| | | |
|---|---|---|
| DE | 197 14 203 | 10/1988 |
| DE | 197 05 402 | 1/1998 |
| DE | 197 51 424 | 11/1998 |
| DE | 103 42 048 | 4/2005 |

\* cited by examiner

*Primary Examiner*—John Fitzgerald
(74) *Attorney, Agent, or Firm*—Kenyon & Kenyon LLP

(57) ABSTRACT

A gas sensor for determining a physical characteristic of a measurement gas, in particular its temperature or the concentration of a gas component in a gas mixture, having a sensor element that has end segments at the side of the measurement gas and at the side of the connection, a sheath that surrounds the sensor element with a radial distance and that has a protective tube, a housing, and a holding cap, and a sealing element that seals the sensor element against the sheath and that is situated on the sensor element between the measurement gas-side end segment and the connection-side end segment of the sensor element. In order to achieve a gas measurement sensor that can be manufactured economically and that has a reduced axial constructive height, and that provides a sufficiently good sealing against the measurement gas, the protective tube is provided at its end facing the sealing element with a tube base that has a central through-opening for the sensor element and that immediately abuts the sealing element, and that presses the sealing element axially between the cap base and the tube base.

21 Claims, 2 Drawing Sheets

GAS SENSOR CONTAINING A PROTECTIVE TUBE

FIELD OF THE INVENTION

The present invention is based on a gas measurement sensor for determining a physical property of a measurement gas, in particular its temperature or the concentration of a gas component in a gas mixture, such as the exhaust gas of an internal combustion engine.

BACKGROUND INFORMATION

In a conventional gas measurement sensor or gas sensor (e.g., German Published Patent Application No. 197 51 424), the housing is turned from a metal blank in which a central longitudinal bore is made. A hexagon is cut onto the outside of the blank, and an outer threading is cut in for the installation of the gas measurement sensor at the measurement location. At the one end of the housing, two collars having different diameters are screwed on in immediate axial succession, and at the other end a collar is screwed on onto which a protective tube is placed and welded, this tube being fashioned as a double tube and having gas through-holes in its tube jacket. A holding cap, fashioned as a deep-drawn part and having an inward-pointing flange, is pushed onto the smaller-diameter collar and is connected to the housing via a weld seam. Between the base of the flange and a radial shoulder formed in the longitudinal bore of the housing, a ceramic molded part is supported, the welding of the holding cap onto the smaller-diameter collar of the housing being carried out under the action of a pressure on the holding cap, so that the ceramic molded part is pressed onto the annular shoulder in the housing. The holding cap is surrounded completely by a concentric protective sleeve that is pushed onto the larger-diameter collar of the housing and is welded onto it. In the end of the protective sleeve facing away from the housing, a cable duct is placed that is caulked in gas-tight fashion to the protective sleeve. In the flange formed in the holding cap, there is situated a sensor element seal that realizes a hermetic separation between the measurement gas chamber enclosed by the protective tube and the reference gas chamber enclosed by the protective sleeve. The sensor element seal is preferably a glass seal made of a melted glass.

In another conventional gas sensor (e.g., German Published Patent Application No. 197 14 203), in a housing fashioned as a solid body with a longitudinal bore, a system of two ceramic molded parts and a seal situated between them, made of a boron nitride-steatite mixture, is placed in the longitudinal bore and is pushed onto the sensor element. The one ceramic molded part is supported on a radial shoulder of the housing that is fashioned in the longitudinal bore, and a holding cap is placed onto the other ceramic molded part; via inward-pointing claws, this cap engages in indentations formed in the housing. When the gas measurement sensor is assembled, an axial force is exerted on the holding cap, for example by a plunger, and this force acts on the seal via the ceramic molded parts and deforms the seal such that the material of the seal is pressed on the one hand against the sensor element and on the other hand against the inside wall of the housing. The segment of the sensor element protruding from the housing at the measurement gas side is surrounded by a protective tube, fashioned as a double tube that, is placed in the end of the housing and is fastened therein.

SUMMARY

The gas measurement sensor or gas sensor according to example embodiments of the present invention provides that a sufficiently good gas seal is achieved between the end segments of the sensor element, which are exposed on the one hand to the measurement gas and on the other hand to a reference gas, for example air, while at the same time a simpler construction of the gas measurement sensor is achieved. Through the design of the protective tube with a base that is used to press the seal and to maintain the pressure tension on the seal, the design of the gas measurement sensor is simplified by the omission of additional ceramic molded parts, so that manufacturing costs are reduced. At the same time, the constructive height of the gas measurement sensor can be significantly reduced by omitting the ceramic molded parts.

The housing and protective cap may be fashioned in one piece as a first deep-drawn part, and the protective tube may be fashioned as a second deep-drawn part having an integrally formed tube base, and a central opening for introducing the sensor element may be provided in the cap base and in the tube base. In this manner, on the one hand a simple and economical manufacture of the sheath is achieved, and on the other hand hotter installation conditions for the gas measurement sensor are made acceptable, because the heat conduction from the hot measurement gas in the direction of the connection side of the sensor element is lower, due to the thin-walled deep-drawn parts and the heat insulation effected by the sealing element.

The first deep-drawn part may be fashioned so as to overlap the second deep-drawn part, and the two deep-drawn parts may be connected to one another in the area of overlap by a circumferential weld seam. The weld seam produces an additional sealing of the connection-side end segment of the sensor element against the measurement gas. If such an additional sealing is omitted, the connection between the deep-drawn parts can also be created by rolling, caulking, or point welding.

On the one hand the protective tube may be fashioned with an integrally formed tube base, and on the other hand the holding cap may be fashioned as a deep-drawn part having a central opening stamped in the tube base or cap base, while the housing is a semi-finished tube. The semi-finished tube is placed with one end segment overlapping each of the two deep-drawn parts, and is fixedly connected to these parts by point welding or by a circumferential weld seam. The circumferential weld seam provides for additional sealing against the measurement gas.

In the following, example embodiments of the present invention are described in more detail on the basis of exemplary embodiments shown in the drawing.

DETAILED DESCRIPTION

Figure 1:
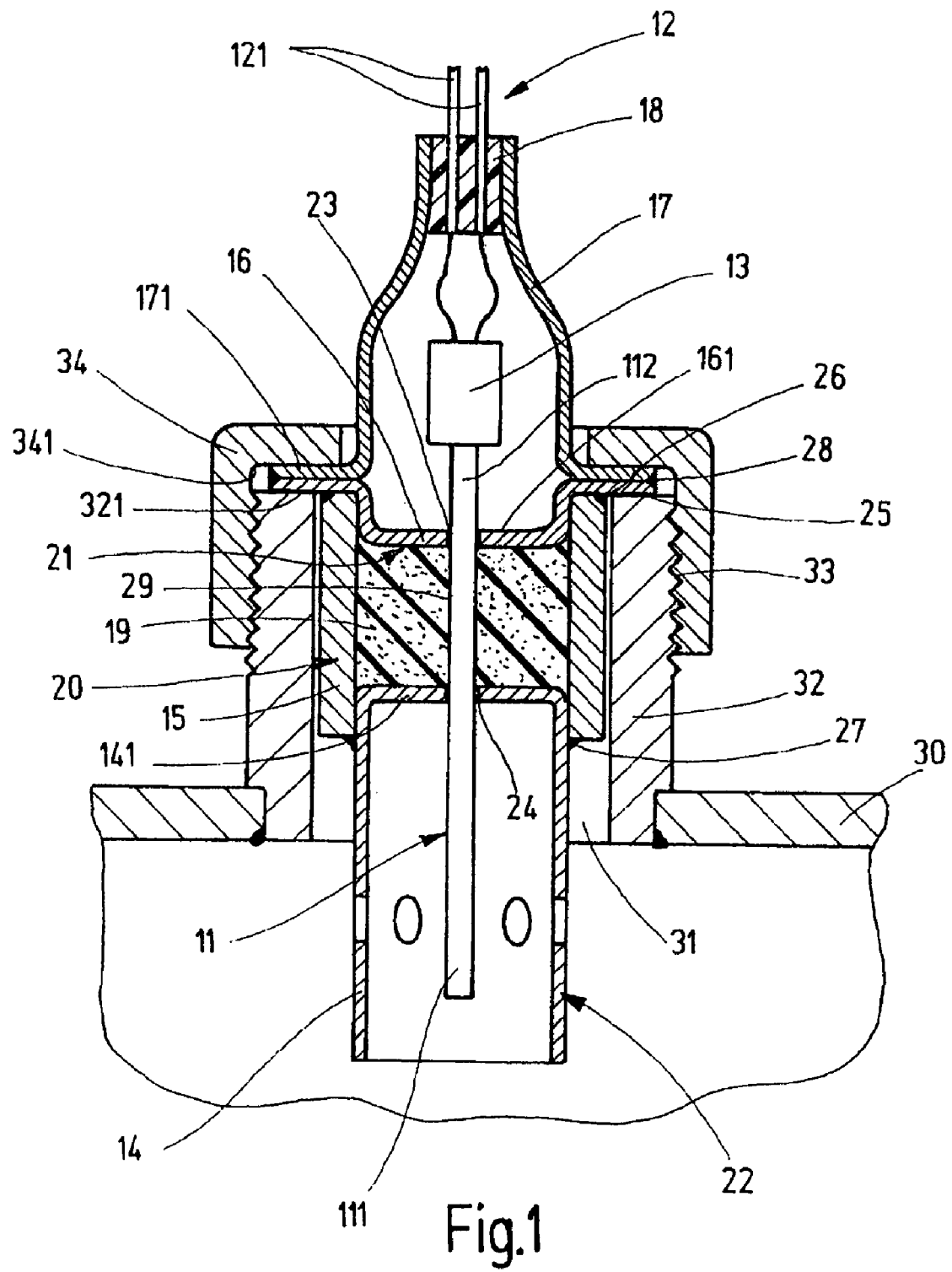
FIG. 1 is a longitudinal cross-sectional view of a gas measurement sensor in its installed position at the location of the measurement gas.

The gas measurement sensor shown schematically in longitudinal section in FIG. 1 is designed as a lambda probe for determining the concentration of oxygen in the exhaust gas of an internal combustion engine. It has a planar sensor element 11 having an end segment 111 at the side of the measurement gas that is exposed to the measurement gas, this end segment being gas-sensitive, and having a connection-side end segment 112 that electrically connects sensor element 11 to an electrical connecting lead 12. In a conventional manner, contact surfaces are situated on connection-side end segment 112 that are connected on the one hand via printed conductors to electrodes situated on end segment 111 at the measurement gas side and on the other hand to connecting conductors 121 of connecting lead 12 via a connecting plug 13. Sensor element 11 is surrounded by a sheath with a radial spacing, this sheath having a protective tube 14, a holding cap 16 that has a central through-opening 23 for sensor element 11 in cap base 161, and a housing 15 situated between protective tube 14 and holding cap 16. Sensor element 11 protrudes from the sheath with its connection-side end segment 112, and is here covered by a protective sleeve 17 that is connected fixedly to the sheath and that is closed at its reduced-diameter end segment by a cable duct 18 that is caulked in gas-tight fashion in protective sleeve 17. Protective tube 14 is closed at its tube end facing holding cap 16 by a one-piece tube base 141 that has a central through-opening 24 for sensor element 11. Between tube base 141 and cap base 161 of holding cap 16, there is situated a sealing element 19, e.g., made of steatite, that presses on the one hand against a segment of sensor element 11 that is situated between measurement gas-side end segment 111 and connection-side end segment 112 of sensor element 11, and on the other hand presses radially against the inside wall of housing 15. The radial pressure force is effected by an axial pressure force that acts on sealing element 19, applied by cap base 161 of holding cap 16 and by tube base 141 of protective tube 14.

In the exemplary embodiment shown in FIG. 1, housing 15 is a semi-finished tube 20, and holding cap 16 is fashioned as deep-drawn part 21, and protective tube 14 with tube base 141 is fashioned as deep-drawn part 22, through-opening 23 or 24 for sensor element 11 being provided in cap base 161 and in tube base 141. An annular flange 25 is integrally formed on at the open end, facing away from cap base 161, of deep-drawn part 21. Deep-drawn part 21 is placed onto the one end of semi-finished tube 20 such that cap base 161 extends into semi-finished tube 20, and annular flange 25 overlaps the annular end of semi-finished tube 20, and protrudes radially past semi-finished tube 20. Semi-finished tube 20 and deep-drawn part 21 are connected fixedly to one another, e.g., by a circumferential weld seam 26. At the other end of semi-finished tube 20, deep-drawn part 22 is placed into semi-finished tube 20 with the application of an axial pressure force on sealing element 19 and is fixedly connected to this semi-finished tube, e.g., via a weld seam 27. Protective sleeve 17 is provided at its end facing deep-drawn part 21 with a one-piece flange 171 that lies on annular flange 25 of deep-drawn part 21 and is fixed thereon, e.g. by a circumferential weld seam 28.

In the exemplary embodiment shown in FIG. 1, deep-drawn part 21 is placed with its flange 25 onto semi-finished tube 20 such that holding cap 16 protrudes into the interior of housing 15. Alternatively, deep-drawn part 21 can also be placed onto semi-finished tube 20 such that holding cap 16 protrudes outward from housing 15.

In order to fasten the gas measurement sensor in exhaust gas pipe 30 of an internal combustion engine, in exhaust gas pipe 30 an opening 31 is provided into which a cylindrical connecting piece 32 is welded. Connecting piece 32 bears on its end facing away from exhaust gas pipe 30 a flat annular surface 321 and an external threaded segment 33. The gas measurement sensor is placed into connecting piece 32, so that annular flange 25 lies on annular surface 321 on first deep-drawn part 21, which forms holding cap 16, and second deep-drawn part 22, which forms protective tube 14, extends into the interior of exhaust gas pipe 30 through opening 31 in exhaust gas pipe 30. A union nut 34, guided over protective sleeve 17, is screwed onto threaded segment 33 of connecting piece 32. Union nut 34 presses with an inner annular surface 341 against flange 171 of protective sleeve 17, and thus presses annular flange 25 on first deep-drawn part 21 onto flat annular surface 321 of connecting piece 32.

The described gas measurement sensor is manufactured according to the following method:

Holding cap 16 with integrally formed annular flange 25 on the one hand, and protective tube 14 with integrally formed tube base 141 on the other hand, are deep-drawn from a sheet that is 0.3-0.6 mm thick. Non-rusting, heat-resistant steels or nickel alloys are used as sheet material. Through-openings 23 and 24 for sensor element 11 are stamped out in, respectively, the center of cap base 161 of first deep-drawn part 21 on the one hand and in the center of tube base 141 of second deep-drawn part 22 on the other hand. As housing 15, a semi-finished tube 20 is used on whose one end first deep-drawn part 21, i.e. holding cap 16 with annular flange 25, is placed and is welded thereto.

Sealing element 19 is manufactured, in a powder-press method, with a central through-duct 29 whose inner cross-section is matched to the cross-section of sensor element 11. If necessary, the end surfaces of sealing element 19 are sintered on in order to prevent powder from trickling out in this area in the assembled state. Sealing element 19 is pushed onto sensor element 11 in the correct position. Sensor element 11 is inserted into housing 15 until sealing element 19 abuts cap base 161 of holding cap 16. Protective tube 14 is then pushed onto sensor element 11 via its through-opening 141 in tube base 141 until its end extends into housing 15 and tube base 141 abuts sealing element 19. A plunger is then inserted into protective tube 14, and a counter-plunger is inserted into holding cap 16, and an axial pressure force is applied between the plunger and a counter-plunger that squeezes sealing element 19, thus creating interior pressure against sensor element 11 and exterior pressure against the inner wall of housing 15. While the pressure force is maintained between the plungers, protective tube 14 is welded onto housing 15 (circumferential weld seam 27). Subsequently, protective sleeve 17, with pre-assembled connecting plug 13 and connecting lead 12 drawn through cable duct 18, is placed onto housing 15, connecting plug 13 being pushed onto measurement gas-side end segment 111 of sensor element 11. Protective sleeve 17 and holding cap 16 are connected fixedly to one another at their flanges 171 and 25, e.g., by laser welding (weld seam 28).

Figure 2:
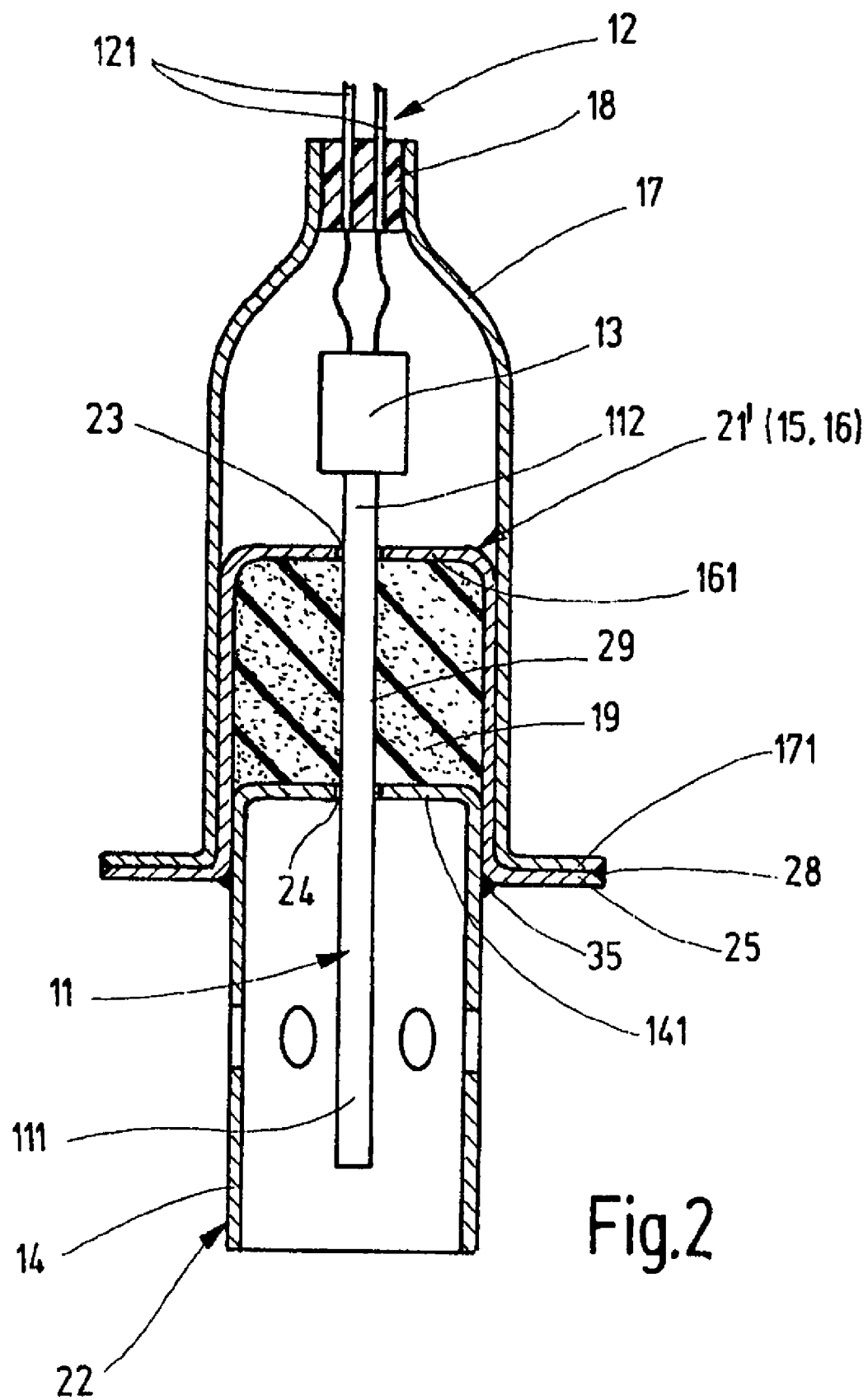
FIG. 2 is a longitudinal cross-sectional view of a gas measurement sensor according to an exemplary embodiment.

The gas measurement sensor shown in longitudinal section as an exemplary embodiment in FIG. 2 differs from the above-described gas measurement sensor in that can 15 and holding cap 16 are fashioned as one-piece deep-drawn part 21' with through-opening 23 for sensor element 11 again stamped out of cap base 161. At the open end of deep-drawn part 21', annular flange 25 is again integrally formed on, and is used as a chuck flange during the installation of the gas measurement sensor at the measurement location, i.e. installation in connecting piece 32 according to FIG. 1, and is fixedly clamped onto connecting piece 32 by union nut 34. Protective tube 14 is fashioned as deep-drawn part 22 in the same manner as in FIG. 1, is pushed into deep-drawn part 21', and is fixedly connected thereto (weld seam 35). Protective sleeve 17 with integrally formed flange 171, fashioned in the same manner as in FIG. 1, is pushed over deep-drawn part 21' and lies with its flange 171 on annular flange 25 fashioned on deep-drawn part 21'. Deep-drawn part 21' and protective sleeve 17 are connected fixedly to one another (weld seam 28) via the two annular flanges 25, 171.

In order to manufacture this gas measurement sensor, protective tube 14 with integrally formed tube base 141 on the one hand, and housing 15 and holding cap 16 with integrally formed annular flange 25 on the other hand, are each deep-drawn in one piece from a sheet that is 0.3-0.6 mm thick, and through-openings 141 and 161 are stamped out in the center of cap base 161 of first deep-drawn part 21' and in the center of tube base 141 of second deep-drawn part 22. Sealing element 19, manufactured in the same manner as described in FIG. 1, is pushed onto sensor element 11 in the correct position and is placed together with sensor element 11 into first deep-drawn part 21', sensor element 11 being guided through through-opening 161 in cap base 161. Subsequently, in the same manner as shown in FIG. 1, second deep-drawn part 22, forming protective tube 14 with tube base 141, is pushed onto sensor element 11 until it extends far enough into first deep-drawn part 21 that tube base 141 abuts sealing element 19. The remaining manufacturing method is the same as described above in connection with FIG. 1; here as well, sealing element 19 is deformed through the application of an axial pressure force by two plungers, and while this pressure force is maintained the two deep-drawn parts 21' and 22 are connected fixedly to one another, e.g., welded to one another (weld seam 35). Circumferential weld seam 35 forms an additional seal against the measurement gas.

Example embodiments of the present invention can also be used in gas measurement sensors that are constructed e.g. as nitrogen oxide sensors that acquire the concentration of nitrogen oxides in the exhaust gas of internal combustion engines, or as temperature sensors for acquiring the exhaust gas temperature.

What is claimed is:

1. A gas measurement sensor for determining a physical property of a measurement gas, comprising:
    a sensor element that has an end segment at a measurement gas side and an end segment at a connection side;
    a sheath that surrounds the sensor element at a radial distance, the sheath having a protective tube, a housing and a holding cap;
    a sealing element that seals the sensor element against the sheath situated on the sensor element between the measurement gas-side end segment of the sensor element and the connection-side end segment protruding axially from the sheath, and pressed by a pressure force directed axially against the holding cap;
    wherein the protective tube is provided on a tube end allocated to the sealing element with a tube base that has a central through-opening for the sensor element and that immediately abuts the sealing element, and the pressing of the sealing element is carried out by the tube base.

2. The sensor according to claim 1, wherein the physical property of the measurement gas includes at least one of (a) a temperature and (b) a concentration of a gas component in a gas mixture.

3. The sensor according to claim 1, wherein the sheath is made of steatite.

4. The sensor according to claim 3, wherein the deep-drawn parts are made of sheets of one of (a) non-rusting, heat-resistant steels and (b) nickel alloys.

5. The sensor according to claim 1, wherein the housing and the holding cap are arranged as a one-piece first deep-drawn part, and the protective tube is arranged with an integrally formed one-piece tube base as a second deep-drawn part, and a central through-opening for introduction of the sensor element is provided in the cap base of the first deep-drawn part and in the tube base of the second deep-drawn part.

6. The sensor according to claim 5, wherein the first deep-drawn part is arranged so as to overlap the second deep-drawn part at its first end, and the two deep-drawn parts are connected fixedly to one another in the overlapping area.

7. The sensor according to claim 6, wherein the two deep-drawn parts are connected fixedly to one another in the overlapping area via a circumferential weld seam.

8. The sensor according to claim 6, wherein an annular flange that acts as a chuck flange during installation of the gas measurement sensor at a location of measurement is integrally formed on the overlap end of the first deep-drawn part.

9. The sensor according to claim 1, wherein the holding cap and the protective tube with integrally formed tube base are each fashioned as a deep-drawn part, and the housing is a semi-finished tube, and a central through-opening for the sensor element is provided in the tube base and in the cap base of each of the two deep-drawn parts.

10. The sensor according to claim 9, wherein the semi-finished tube overlaps with its one end the one deep-drawn part and overlaps with its other end the other deep-drawn part, and is fixedly connected to the deep-drawn parts in the overlapping areas by a circumferential weld seam in each case.

11. The sensor according to claim 9, wherein the semi-finished tube overlaps with its one end the one deep-drawn part and overlaps with its other end the other deep-drawn part, and is fixedly connected to the deep-drawn parts in the overlapping areas.

12. The sensor according to claim 11, wherein an annular flange that acts as a chuck flange during installation of the measurement gas sensor at a measurement location is integrally formed on the open end of the deep-drawn part that forms the holding cap, the flange protruding radially past a circumference of the semi-finished tube.

13. A method for manufacturing a gas measurement sensor for determining at least one of (a) a physical characteristic of a measurement gas, (b) its temperature and (c) a concentration of a gas component in a gas mixture, having a sensor element that has an end segment at a measurement gas side and an end segment at a connection side, having a sheath that surrounds the sensor element at a radial distance and that is made up of a protective tube, a housing, and a holding cap, and having a sealing element that seals the sensor element against the sheath, comprising:
    deep-drawing in one piece from a sheet the housing and holding cap and the protective tube having an integrally formed tube base;
    centrally stamping out a through-opening in the cap base of a first deep-drawn part and in the tube base of a second deep-drawn part;
    pushing the sensor element with sealing element pushed on in a correct position through the central through-opening in the cap base of the first deep-drawn part until the sealing element abuts the cap base of the first deep-drawn part;
    pushing the second deep-drawn part via the through-opening in its tube base, onto the sensor element until it extends into the first deep-drawn part and the tube base abuts the sealing element;
    axially pressing the sealing element by two plungers, acting on the tube base of the first deep-drawn part and on the cap base of the second deep-drawn part; and
    while pressure forces are in effect, fixedly connecting the two deep-drawn parts (to one another.

14. The method according to claim 13, wherein the fixedly connecting includes welding.

15. The method according to claim 13, wherein during the deep drawing process an annular flange is integrally formed on an end, facing away from the cap base, of the first deep-drawn part.

16. The method according to claim 13, wherein the deep-drawn parts are drawn from a sheet that is 0.3-0.6 mm thick of one of (a) a non-rusting, heat-resistant steel and (b) a nickel alloy.

17. The method according to claim 13, wherein the sealing element is manufactured using a powder-press method, with a central through-duct whose inner cross-section is matched to an cross-section of the sensor element.

18. The method according to claim 17, wherein the end surfaces of the sealing element are sintered on.

19. A method for manufacturing a gas measurement sensor for determining at least one of (a) a physical characteristic of a measurement gas, (b) its temperature and (c) a concentration of a gas component in a gas mixture, having a sensor element that has an end segment at a measurement gas side and an end segment at a connection side, having a sheath that surrounds the sensor element at a radial distance and that is made up of a protective tube, a housing, and a holding cap, and having a sealing element that seals the sensor element against the sheath, comprising:

deep-drawing a holding cap and a protective tube having an integrally formed tube base from a sheet;

centrally stamping a through-opening out in the cap base of a first deep-drawn part and in the tube base of the second deep-drawn part;

placing the first deep-drawn part, forming the holding cap, onto one end of a semi-finished tube used as a housing and is fixedly connecting it thereto;

pushing the sensor element with the sealing element pressed onto it in a correct position through the central through-opening in the cap base of the first deep-drawn part until the sealing element abuts the cap base of the first deep-drawn part;

pushing the second deep-drawn part through the through-opening in its tube base onto the sensor element until it extends into the housing and the tube base abuts the sealing element;

axially pressing the sealing element by two plungers, acting on the tube base of the first deep-drawn part and on the cap base of the second deep-drawn part; and while pressure forces are in effect, fixedly connecting the two deep-drawn parts to one another.

20. The method according to claim 19, wherein the fixedly connecting includes welding.

21. The method according to claim 19, wherein during the deep-drawn drawing process, an annular flange is integrally formed on an end, facing away from the cap base, of the deep-drawn part.

* * * * *